United States Patent
Harris, Jr. et al.

(10) Patent No.: US 9,703,379 B2
(45) Date of Patent: Jul. 11, 2017

(54) SYSTEMS AND METHODS FOR MULTIMEDIA TACTILE AUGMENTATION

(71) Applicants: Ralph Alan Harris, Jr., Houston, TX (US); Uduak Udomon, Houston, TX (US)

(72) Inventors: Ralph Alan Harris, Jr., Houston, TX (US); Uduak Udomon, Houston, TX (US)

(73) Assignee: XSYNC TECHNOLOGIES LLC, Houston, TX (US)

( * ) Notice: Subject to any disclaimer, the term of this patent is extended or adjusted under 35 U.S.C. 154(b) by 424 days.

(21) Appl. No.: 14/295,471

(22) Filed: Jun. 4, 2014

(65) Prior Publication Data
US 2015/0057493 A1 Feb. 26, 2015

Related U.S. Application Data

(60) Provisional application No. 61/868,039, filed on Aug. 20, 2013.

(51) Int. Cl.
| | |
|---|---|
| A61F 5/00 | (2006.01) |
| G06F 3/01 | (2006.01) |
| A61H 19/00 | (2006.01) |
| A61B 34/00 | (2016.01) |
| A63F 13/24 | (2014.01) |
| G06F 17/30 | (2006.01) |
| G11B 27/10 | (2006.01) |
| G11B 31/00 | (2006.01) |
| G06F 21/31 | (2013.01) |

(52) U.S. Cl.
CPC ............. *G06F 3/016* (2013.01); *A61B 34/76* (2016.02); *A61H 19/00* (2013.01); *A63F 13/24* (2014.09); *G06F 17/30023* (2013.01); *G06F 17/30864* (2013.01); *G11B 27/10* (2013.01); *G11B 31/00* (2013.01); *A61H 2201/501* (2013.01); *A61H 2201/5023* (2013.01); *A61H 2201/5048* (2013.01); *G06F 21/31* (2013.01)

(58) Field of Classification Search
CPC .......... A61H 19/30; A61H 19/00; G06F 3/016
USPC .................................. 600/38–41; 340/407.1
See application file for complete search history.

(56) References Cited

U.S. PATENT DOCUMENTS

| | | | |
|---|---|---|---|
| 6,300,936 | B1 | 10/2001 | Braun et al. |
| 6,368,268 | B1 | 4/2002 | Sandvick et al. |
| 7,791,588 | B2 | 9/2010 | Tierling et al. |
| 8,378,794 | B2 | 2/2013 | Alarcon |

(Continued)

FOREIGN PATENT DOCUMENTS

| | | |
|---|---|---|
| CN | 102184419 B | 5/2013 |
| WO | 2013096327 | 6/2013 |

*Primary Examiner* — John Lacyk
(74) *Attorney, Agent, or Firm* — Hahn Loeser & Parks, LLP (57) ABSTRACT

The present disclosure described methods and systems for multimedia tactile augmentation. At least one method includes identifying media content loaded on a first computer, locating instructions stored on a second computer (said instructions corresponding to the content), initiating playback of the content, and synchronizing the instructions with the content. Said method further includes parsing and converting the instructions into one or more electrical signals, driving one or more haptic feedback devices with the electrical signals in synchronization with the playback of the content, and presenting the content to the user. The haptic feedback devices provide physical stimulation to a user accessing the content.

12 Claims, 11 Drawing Sheets

(56) References Cited

U.S. PATENT DOCUMENTS

| | | |
|---|---|---|
| 8,572,293 B2 | 10/2013 | Cruz-Hernandez et al. |
| 8,909,817 B2 | 12/2014 | Cruz-Hernandez et al. |
| 9,064,385 B2 | 6/2015 | Saboune et al. |
| 2002/0138562 A1 | 9/2002 | Wies et al. |
| 2008/0223627 A1 | 9/2008 | Lacroix et al. |
| 2009/0096632 A1 | 4/2009 | Ullrich et al. |
| 2012/0304216 A1 | 11/2012 | Strong |
| 2013/0038792 A1 | 2/2013 | Quigley et al. |

FIGURE 1

SYSTEMS AND METHODS FOR MULTIMEDIA TACTILE AUGMENTATION

CROSS-REFERENCE TO RELATED APPLICATIONS

This application claims priority to and the benefit of U.S. Patent App. 61/868,039 filed on Aug. 20, 2013, the disclosure of which is incorporated herein by reference in its entirety.

BACKGROUND AND SUMMARY

The present disclosure relates to systems and methods for augmenting multimedia experiences with tactile sensations.

The computing industry has trended towards the convergence of online content and hardware-connected components since the inception of the World Wide Web. Only recently, however, has this trend begun to include haptic devices. As of the writing of this patent, a number of inventions have been disclosed that address the intersection between multimedia and locally-connected hardware devices. For example, U.S. Pat. No. 6,368,268 to Hassex, Inc. ("Hassex") shows an invention that is capable of synchronizing sensations between a user interface and a sexually-oriented hardware-connected device.

Various User Interfaces exist, including: a sexually-oriented hardware device receiving uni-directional control signals from a hand-operated controller, such as a joystick; two sexually-oriented hardware devices, both of which send simultaneous, bi-directional control signals based on real-time usage; and a server that sends control signals directly to a remote software interface, which sends the control signal to the sexually-oriented hardware device. For example, Hassex specifies that the control signal, which is received via a data packet, is first decoded by the user interface then sent through the I/O port of the computer to the locally-connected, sexually-oriented hardware device.

Similarly, U.S. Pat. No. 8,378,794 to Internet Services, LLC ("Inet Svcs") describes a hardware component and its interactions with multimedia files that are associated with hardware control signals. The hardware device generates sensations in response to the hardware control signals via a belt system. The RealTouch™ device described by Inet Svcs uses a static Web portal to serve users multimedia files containing embedded hardware control signals. A user's computer receiving the files includes a software add-on for Windows Media Player that decodes the control signals. Once the software add-on is installed and the multimedia file is downloaded, Windows Media Player simultaneously plays the multimedia file and decrypts, then plays the associated hardware control signals directly from the user's computer.

Presently disclosed is a method for multimedia tactile augmentation. In embodiments, the method includes identifying media content loaded on a first computer; locating instructions stored on a second computer, said instructions corresponding to the content; initiating playback of the content; synchronizing the instructions with the content; parsing and converting the instructions into one or more electrical signals; driving one or more haptic feedback devices with the electrical signals in synchronization with the playback of the content, said haptic feedback devices providing physical stimulation to a user accessing the content; and presenting the content to the user.

In some embodiments, the parsing and synchronizing are performed by the first computer and the converting is performed by a processing unit coupled to the haptic feedback devices.

In some embodiments, the parsing, synchronizing and converting are performed by a processing unit coupled to the haptic feedback devices.

In some embodiments, the parsing and synchronizing are performed by the second computer and the converting is performed by a processing unit coupled to the haptic feedback devices.

In some embodiments, the method further includes the second computer providing access to the instructions via the Internet through a web interface presented on the first computer.

In some embodiments, the method further includes the content with computer vision to determine a playback time of the content and synchronizing the instructions with the content based on the determined playback time.

Also disclosed is a method for multimedia tactile augmentation that includes identifying media content within a first file loaded on a computer; locating instructions within a second file loaded on the computer, said instructions corresponding to the content; initiating playback of the content; synchronizing the instructions with the content; parsing and converting the instructions into one or more electrical signals; driving one or more haptic feedback devices with the electrical signals in synchronization with the playback of the content, said haptic feedback devices providing physical stimulation to a user accessing the content; and presenting the content to the user.

Also disclosed is a haptic feedback system. The haptic feedback system includes a processor coupled to a memory, the processor configured to execute the following computer-executable instructions stored in the memory: synchronizing media content loaded on a first computer with instructions received from a second computer, said instructions corresponding to the media content, and converting the instructions into one or more electrical signals; and at least one haptic feedback device in communication with the processor, wherein the at least one haptic feedback device is configured to receive the one or more electrical signals and to provide physical stimulations to a user accessing the content in synchronization with the playback of the media content.

In some embodiments, the haptic feedback system further includes a presentation device adapted to present the media content to the user.

In some embodiments, the at least one haptic feedback device is further configured to communicate wirelessly with the processor.

In some embodiments, the at least one haptic feedback device further comprises at least one communication device selected from the group consisting of a serial port, a parallel port, a universal serial bus, a BlueTooth device, a near field communication device, and an infrared communication device.

In some embodiments, the at least one haptic feedback device is a game controller adapted for use with an online video game system.

In some embodiments, wherein the at least one haptic feedback device is a sexually oriented hardware device.

BRIEF DESCRIPTION OF THE DRAWINGS

A better understanding of the various disclosed embodiments can be obtained when the following detailed description is considered in conjunction with the attached drawings, in which.

It should be understood that the drawings and corresponding detailed description do not limit the disclosure, but on the contrary, they provide the foundation for understanding all modifications, equivalents, and alternatives falling within the scope of the appended claims.

DETAILED DESCRIPTION

The disclosed embodiments relate to the synchronization of locally-connected hardware components to online, web-based multimedia events such as online movies, interactive video games, entertainment media and/or other non-entertainment media. More specifically, the disclosed embodiments relate to software and systems executing the software that create the user-experienced haptic synchronization effect between various online video sources and locally-connected haptic hardware components. The disclosed embodiments rely on a client-server architecture to maintain synchronization between locally-connected haptic hardware and online multimedia events. These embodiments synchronize two separate data sources: online multimedia being served from a content provider's website, such as YouTube, Netflix, or Amazon Instant Video; and haptic hardware instructions associated with said multimedia and hardware device being served by a web infrastructure configured to support said embodiments. In contrast to prior systems, the separation of the multimedia content and the haptic hardware instructions improves the utility of the presently disclosed systems and methods by enabling rapid deployment of instructions for new media content and new haptic hardware. In this manner, media content may be synchronized with haptic hardware instructions for both pre-existing devices as well as new devices without modification or alternation of the media content. This flexibility and scalability was not possible with prior systems, such as those discussed above, in which hardware control signals were embedded directly in multimedia files.

The paragraphs that follow describe in detail various examples of the above-described embodiments. An example of local software executing on a user's local client computer system is first described, followed by a description of an illustrative Web infrastructure and a description of an illustrative local hardware device. Three illustrative embodiments are then described, wherein the multimedia event's hardware instruction set is interpreted by a different component for each embodiment (i.e., the local client computer, the local hardware device and the Web infrastructure).

Web Infrastructure

Figure 1:
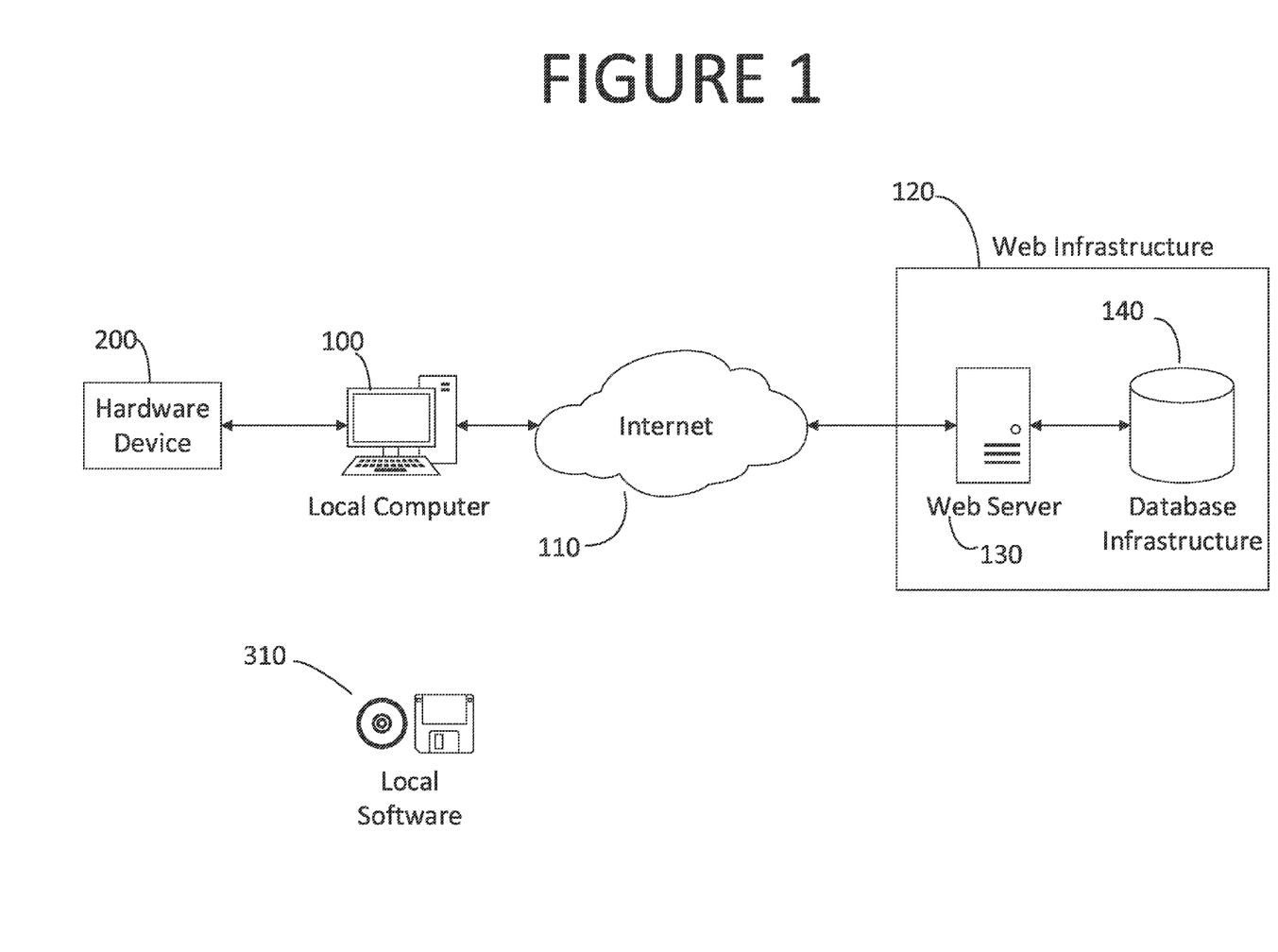
FIG. 1 shows a system diagram that includes an illustrative Web Infrastructure.

FIG. 1 shows an overview of an illustrative embodiment of a multimedia tactile augmentation system that includes the Web Infrastructure 120, an Internet 110 infrastructure with one or more Web Server 130 and Database Infrastructure 140. In the embodiment shown, a Web Server 130 responds to requests from the Local Software 310 executing on Local Computer 100 or from the Local Hardware Device 200, and further queries the Database Infrastructure 140 as needed. Local Software 310 may be stored on non-volatile information storage medium as shown, or may be downloaded onto the Local Computer 100 via, e.g., the Internet 110.

The core functionalities of the Web Infrastructure 120 include, but are not limited to:
1. Responding to requests from the Local Software 310 or Local Hardware Device 200;
2. Maintaining User account information; and
3. Hosting any web sites required to support the disclosed system.

Local Hardware Device

Figure 2:
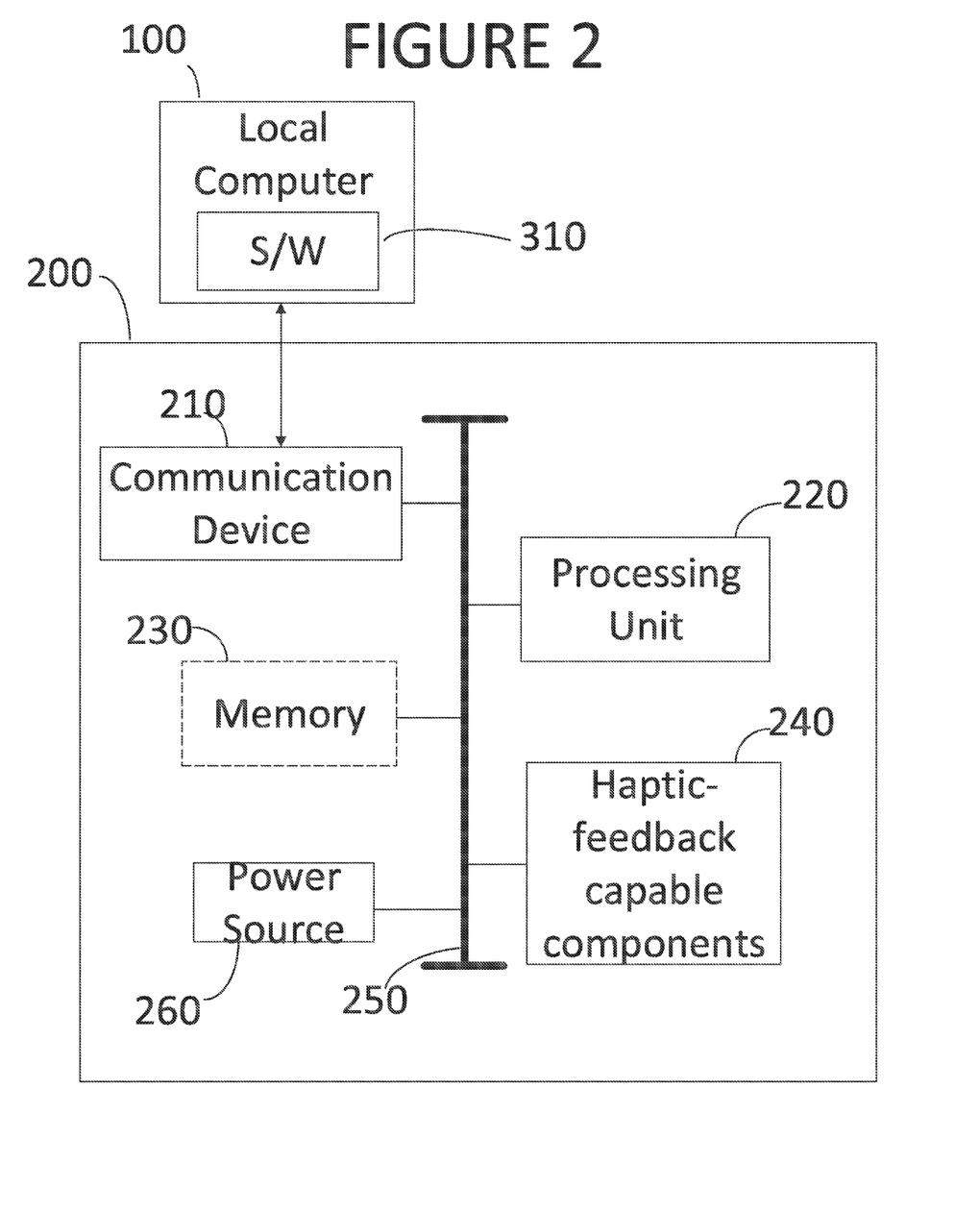
FIG. 2 shows a block diagram of a Local Hardware Device.

FIG. 2 shows a preferred embodiment of the Local Hardware Device 200 that includes a Communication Device 210, a Processing Unit 220, one or more Haptic Feedback Capable Components 240, such as vibration motors, a Power Source 260, such as a battery or a port for electrical port connectivity, and a Bus 250 which is used to transport communications between each of the Local Hardware Device's 200 components. The Local Hardware Device 200 may exist in any shape or size, with the distinguishing factor being that it is designed to work with the disclosed system. In at least some illustrative embodiments, multiple Local Hardware Devices 200 are coupled to local computer 100 and are simultaneously operable. In at least some illustrative embodiments, the Haptic Feedback Capable components 240 of local hardware device 200 provide physical and/or sexual stimulation to one or more users of the disclosed system(s).

The core functionalities of the Local Hardware Device 200 may include, but are not limited to:
1. Establishing connectivity to the personal computing environment via the Communication Device 210; examples of the Communication Device 210 include, but are not limited to:
    a. Serial and parallel ports, Universal Serial Bus (USB), BlueTooth, Near Field Communications (NFC) or other wireless technologies;
2. Establishing connectivity to the Local Software 310 or Web Infrastructure 120;
3. Responding to requests for identifying information;
4. Interacting with instructions:
    a. The Processing Unit 220 may receive instructions via the Web Infrastructure 120 or the Local Software 310; and
    b. The instructions may be processed before the Processing Unit 220 receives them;
        i. If the instructions are not processed before the Processing Unit 220 receives them, the Processing Unit 220 may process the instructions, possibly including the temporary storage of processed instructions in the Locally Connected Hardware's 200 Memory 230; and
5. Interacting with the Haptic Feedback Capable Components 240:
    a. The processing unit commands each Haptic Feedback Capable Component 240 to respond for specific durations and in specific patterns based on the instructions, with the end result being synchronization between the Local Hardware Device's 200 Haptic Feedback Capable Components 240 and the online multimedia event.

Local Software

In at least some illustrative embodiments, Local Software 310 executes on a Local Computer 100 in the form of a browser extension or add-on. This enables the Local Software 310 to enhance an existing web browser such as, e.g., Microsoft Internet Explorer, Google Chrome or Mozilla Firefox by adding the functionalities of the Local Software 310 to the existing web browser.

The core functionalities of the Local Software 310 include, but are not limited to:

1. Establishing and maintaining connectivity to and interactivity with the Web Infrastructure 120:
   a. Facilitating User authentication to the Web Infrastructure 120;
   b. Facilitating User authentication for multiple accounts simultaneously;
   c. Sending identifying information about multimedia to the Web Infrastructure 120 to determine if the detected multimedia has an associated hardware instruction set; if the associated hardware instruction set exists, designating the multimedia as supported;
   d. Retrieving associated hardware instruction sets;
2. Interacting with the Local Hardware Device 200:
   a. Establish and maintain connectivity to the Local Hardware Device 200;
   b. Retrieve identifying information about the Local Hardware Device 200;
   c. Determine if the Local Hardware Device 200 is associated with the authenticated User's account; if not, facilitate account interactions with the Web Infrastructure 120 to associate the Local Hardware Device 200 with the User's account, or facilitate authentication to the correct account to permit usage of the Local Hardware Device 200;
   d. Sending instructions to the Local Hardware Device 200;
   e. Monitoring playback of Local Hardware Device 200 as needed to maintain synchronization between Local Hardware Device 200 and multimedia event;
3. Interacting with web pages:
   a. Parsing webpages to detect multimedia;
   b. Detecting identifying information about the multimedia;
   c. Manipulating the displayed web page to label discovered multimedia as supported or not, based on feedback from the Web Infrastructure 120;
   d. Manipulating the multimedia player to facilitate interaction with multimedia;
4. Interacting with multimedia on web pages:
   a. Controlling the playback of multimedia to facilitate synchronization between the Local Hardware Device 200 and the multimedia; and
   b. Identifying and controlling the current playback time of multimedia to facilitate synchronization between the Local Hardware Device 200 and the multimedia.
   c. Analyzing the multimedia content with computer vision to determine a playback time of the multimedia content and synchronizing the instructions for the Local Hardware Device 200 with the multimedia content based on the determined playback time.

Alternate embodiments of the Local Software 310 may include, but are not limited to:

1. A component of a completely custom application, such as an application designed for a mobile platform, tablet, wearable device, or other, similar personal computing environments;
2. A multi-component system of applications that interact and operate to deliver the same functionality of a single browser add-on or extension; examples include a desktop application that facilitates User authentication and hardware communications and interacts with a web browser add-on or extension that facilitates interactivity with a web page, multimedia, and the Web Infrastructure 120; and
3. A fully-enclosed web application that facilitates all functions across a network via a web server; said Web Server 130 may exist in various forms, such as on a standalone hardware device, on the Local Hardware Device 200, or as a component within a cloud infrastructure environment.

The disclosed systems and methods are best understood when described in an illustrative usage context. To this end, the paragraphs that follow describe three illustrative embodiments, wherein for each embodiment the multimedia event's hardware instruction set is interpreted by a different component.

First Illustrative Embodiment

Figure 3A:
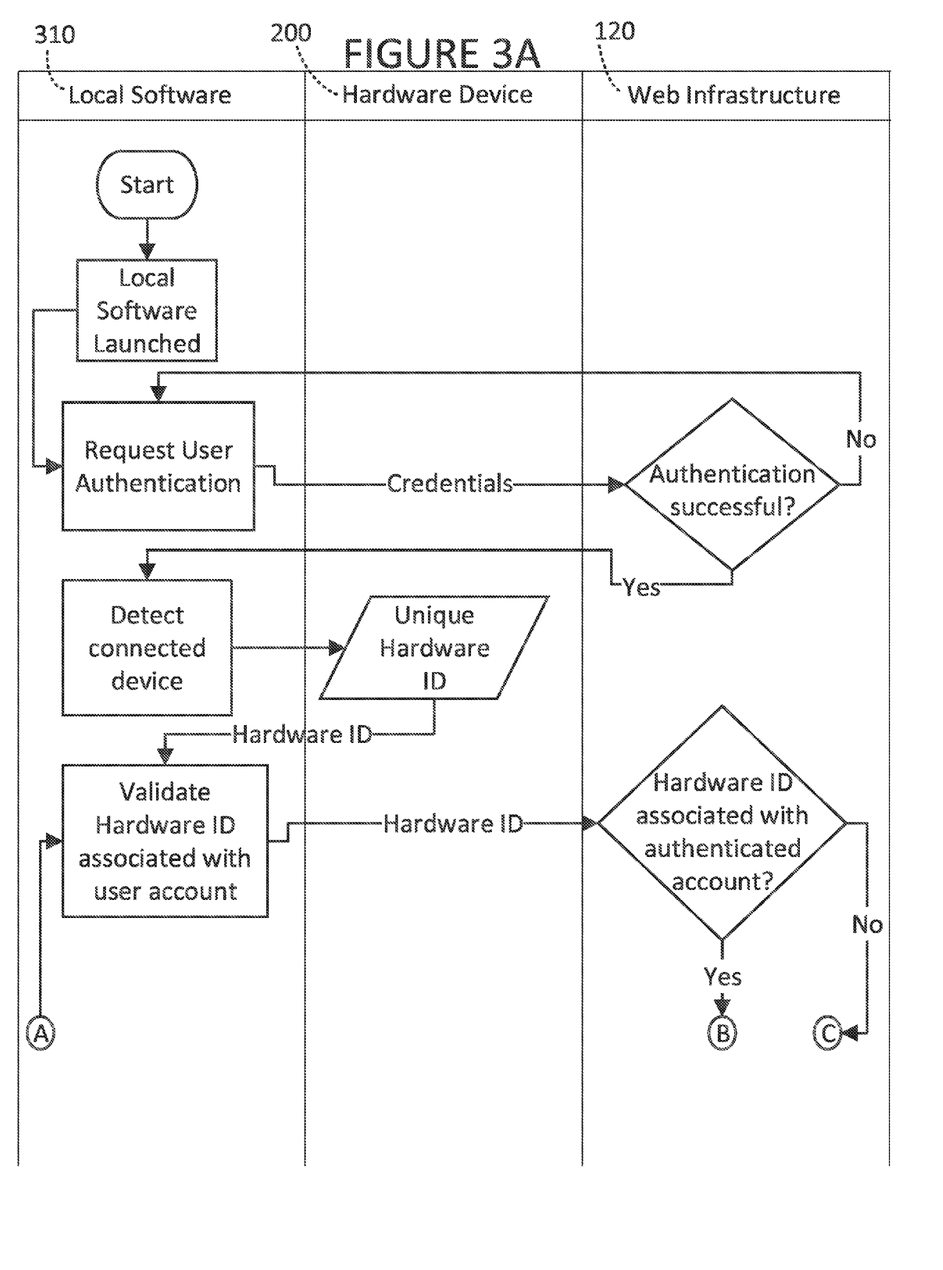
FIGS. 3A-3C show a software flowchart and functional distribution for a first illustrative embodiment.
Figure 3B:
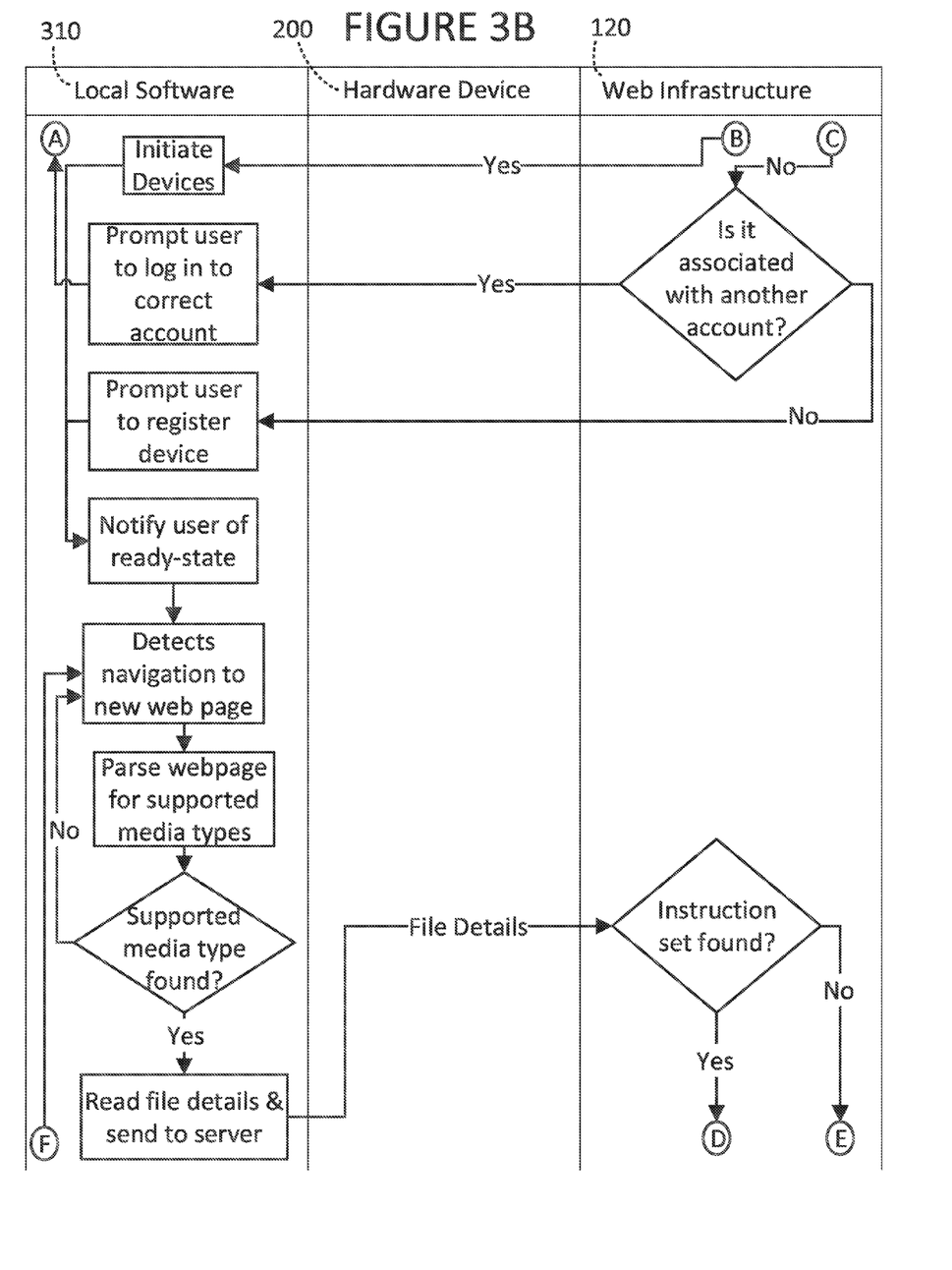
Figure 3C:
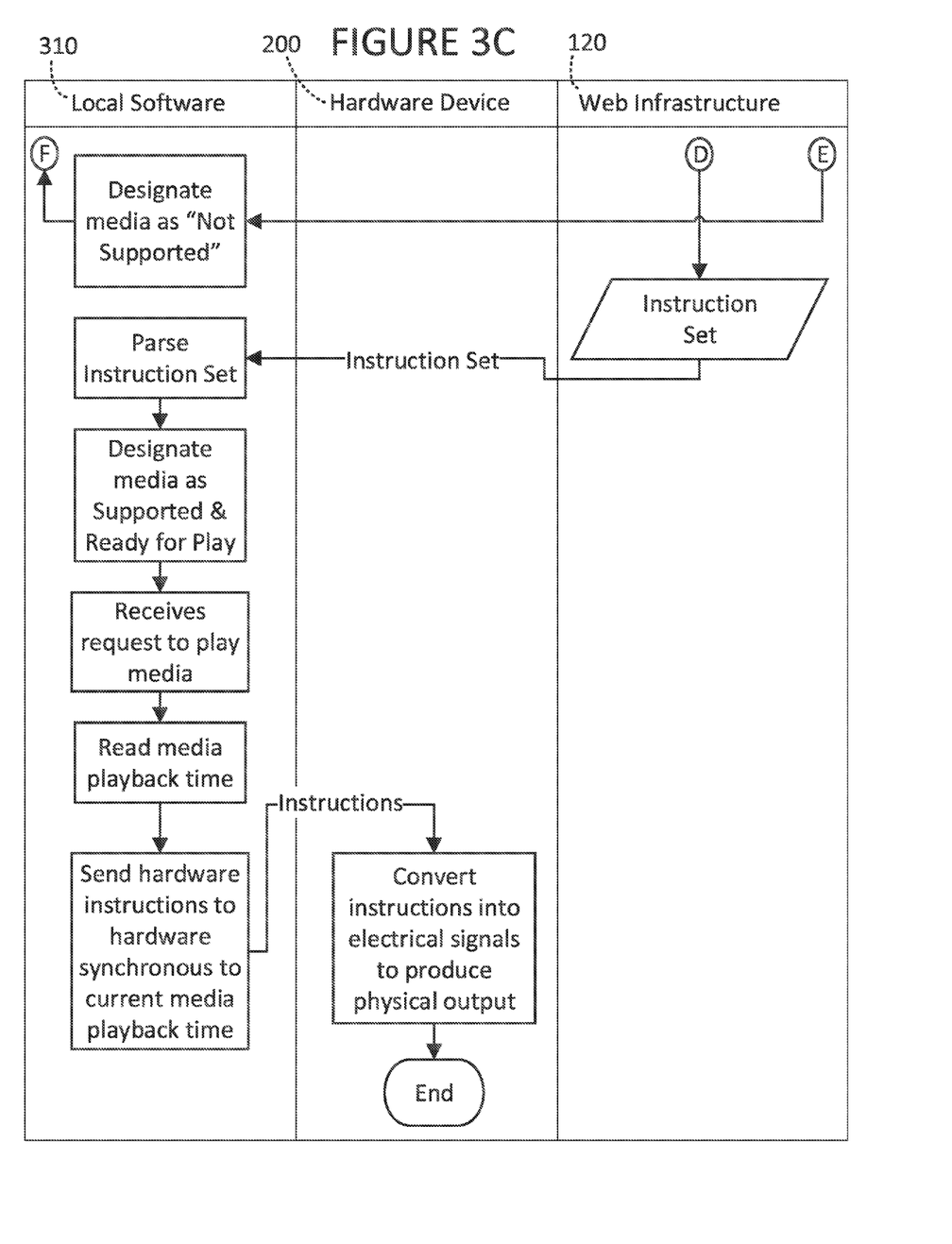

FIG. 3 shows a beginning-to-end illustrative process view of the disclosed systems and methods, wherein the instruction set processing occurs within the Local Software 310.

A User connects the Local Hardware Device 200 to the Local Computer 100 via the Local Hardware Device's 200 Communication Device 210. Once the Local Hardware Device 200 is connected to the Local Computer 100, the User launches the Local Software 310. The Local Software 310 will prompt the User to log in to their account; if an account has not been established, the User is prompted to create a new account. Credentials are passed from the Local Software 310 to the Web Infrastructure 120, which validates the authentication attempt.

Once authenticated, the Local Software 310 detects the Local Hardware Device 200, requests the Local Hardware Device's 200 unique hardware ID, and verifies with the Web Infrastructure 120 that the specific Local Hardware Device 200 is associated with a currently-authenticated account. If so, the Local Software 310 initiates the Local Hardware Device 200. When initialized, the Local Hardware Device 200 is ready to receive instructions from the Local Software 310 and the User is notified that the Local Hardware Device 200 is ready for use.

If the unique hardware ID is not associated with an authenticated account, the Web Infrastructure 120 checks to see if it is associated with another account. If it is, the Local Software 310 prompts the User to log in to the correct account to be able to use the connected device; in at least some illustrative embodiments, the usage of simultaneous multiple account logins may be allowed to permit the usage of multiple devices. If the unique hardware ID is not associated with any accounts, the User is prompted to register the unique hardware ID with their account. Once the Local Hardware Device 200 is registered or the User is authenticated to the correct account, the Local Software 310 verifies again with the Web Infrastructure 120 that the specific Local Hardware Device 200 is associated with a currently-authenticated account. The Local Software 310 then initiates the Local Hardware Device 200 and notifies the User that the Local Hardware Device 200 is ready for use.

The User then uses the Local Software 310 to navigate to a web page. Each time a new web page is loaded, the Local Software 310 parses the page to detect supported media. If supported media is not found, the Local Software 310 does nothing; if supported media is found, the Local Software 310 detects and sends the media file information to the Web Infrastructure 120. The Web Infrastructure 120 queries the Database Infrastructure 140 to determine if a hardware instruction set exists for the detected media. If an instruction set is not found, the Local Software 310 designates the media as "not supported;" if an instruction set is found, the Local Software 310 designates the media as "supported & ready for play," and the instruction set file is downloaded to the Local Software 310 for parsing and playback. The designation of "supported & ready for play" and "not supported" may exist as a visual indicator on or near the media file within the web page.

The User then plays the media. The Local Software 310 reads the current playback time of the media and sends the hardware instruction set to the Local Hardware 200 synchronous to the current media playback time. The hardware instruction set contains time flags to mark the accurate playback time of the Haptic Feedback Capable Components 240; the Local Software 310 monitors the accurate playback time of the media event and uses both pieces of information to maintain synchronization of the Haptic Feedback Capable Components 240 on the Local Hardware 200 and the media. If the current playback time of the media is adjusted by the User, the Local Software 310 uses the updated current playback time and the time flags in the hardware instruction set to re-establish synchronization based on the adjustment made by the User. The playback time of the media may be access from the media player, the operating system, the media file, or any other location from which a playback time may be accessed.

In another embodiment, the Local Software 310 includes a computer vision component adapted to analyze the content of the media. The computer vision component may determine a playback time of the media based on the analyzed content. In some embodiments, the computer vision component may analyze one or more frames of the media content, and analyzed frames may be used as an index to the media to determine the playback time. In this manner, the playback time may be either a time index or another index to the media content capable of being associated with the instructions to synchronize the hardware instructions with the playback of the media content. The computer vision component may be a software component stored in memory and executed on a processor of a haptic feedback system.

When the Local Hardware 200 receives the instructions from the Local Software 310, the Local Hardware 200 interprets said instructions and generates corresponding electrical signals that are sent to the Haptic Feedback Capable Components 240, resulting in the production of physical haptic feedback output that is experienced by the User.

When the User stops the playback of the media the Local Software stops the playback of the instruction set to the Local Hardware 200, which stops sending electrical signals to the Haptic Feedback Capable Components 240. The system is then ready for navigation to the next web page, or, if the User disconnects the Local Hardware 200, all memory is cleared and the Local Software 310 is rendered dormant until the Local Hardware 200 is connected again.

Second Illustrative Embodiment

Figure 4A:
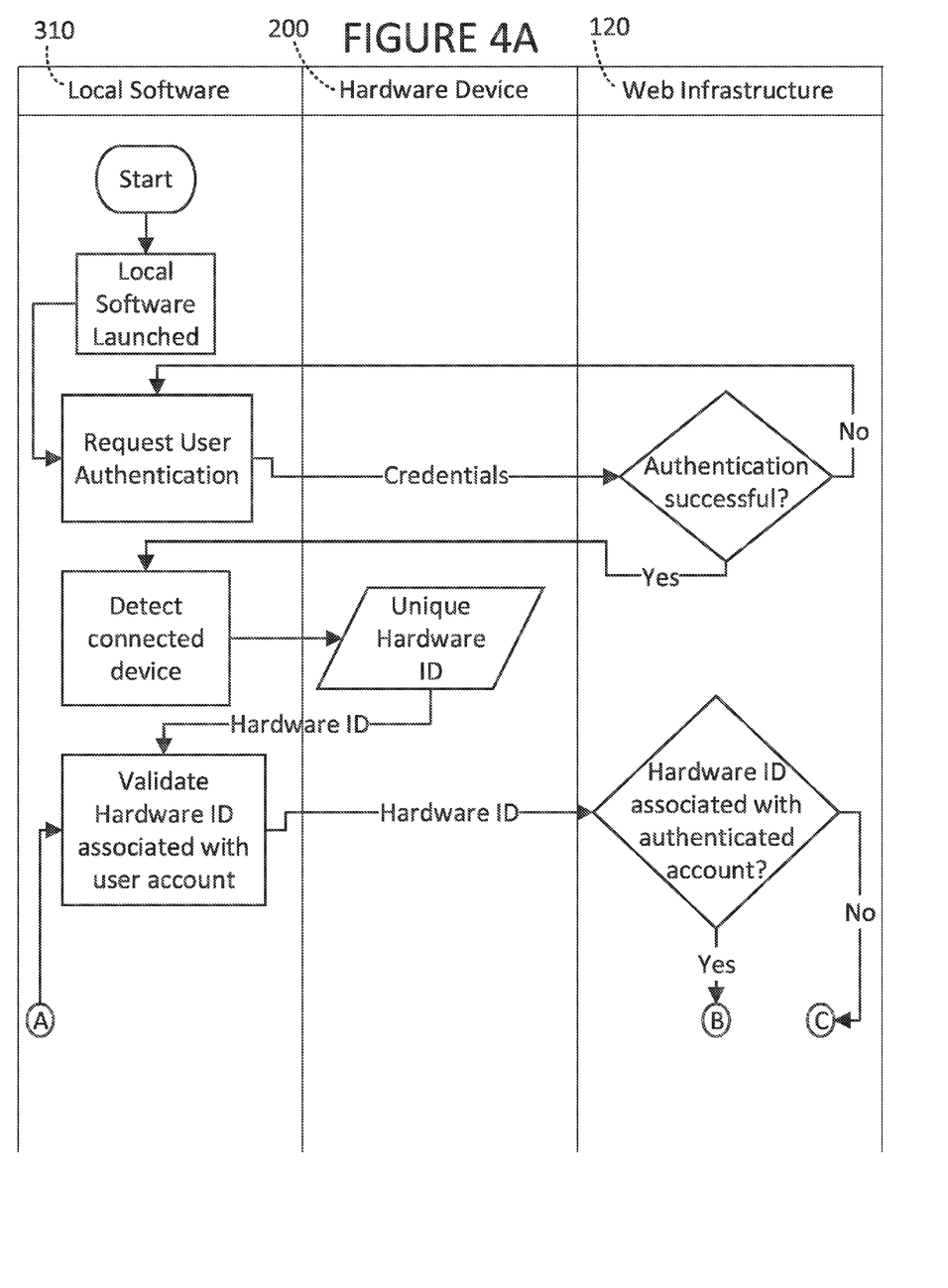
FIGS. 4A-4C show a software flowchart and functional distribution for a second illustrative embodiment.
Figure 4B:
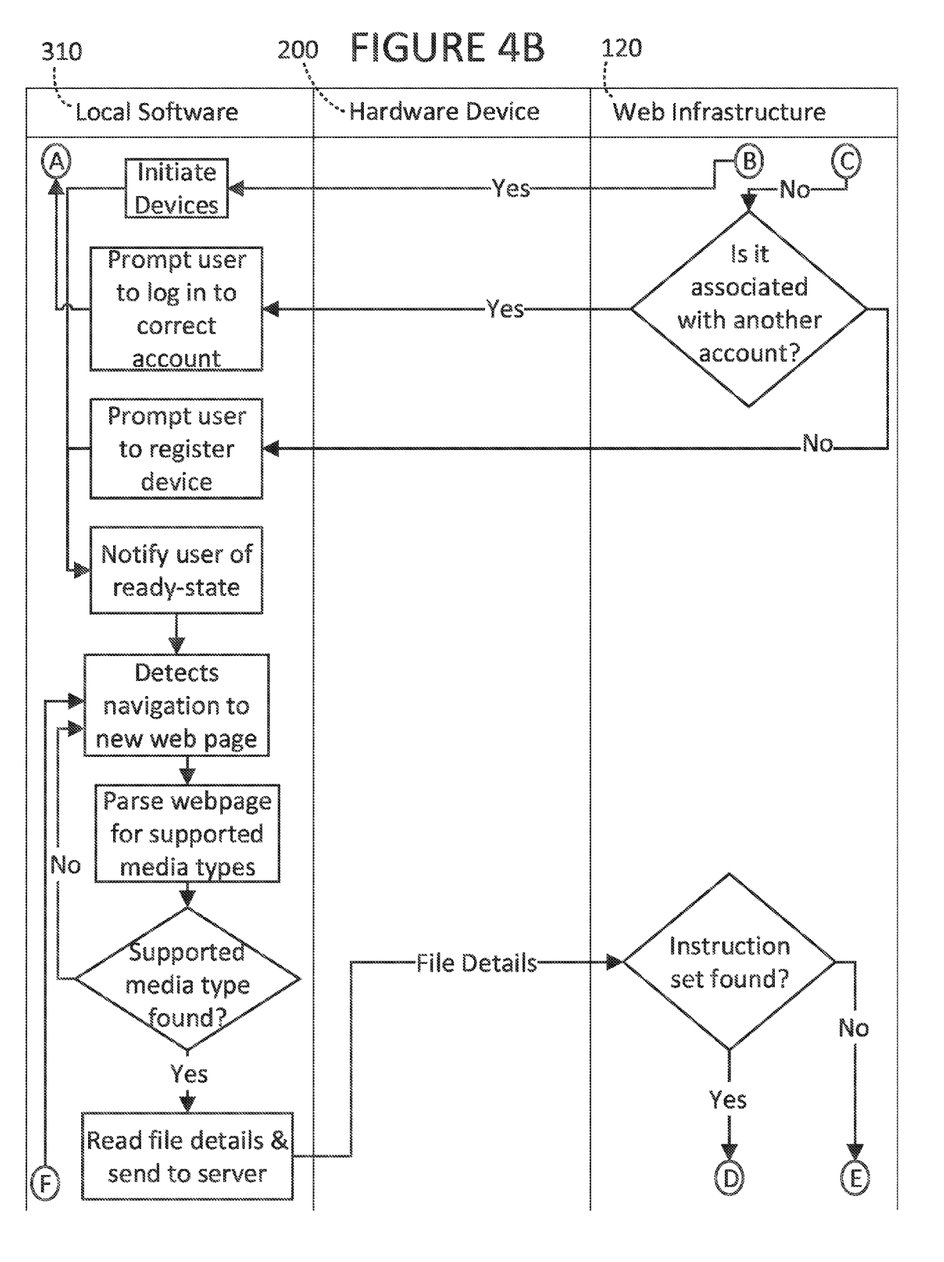
Figure 4C:
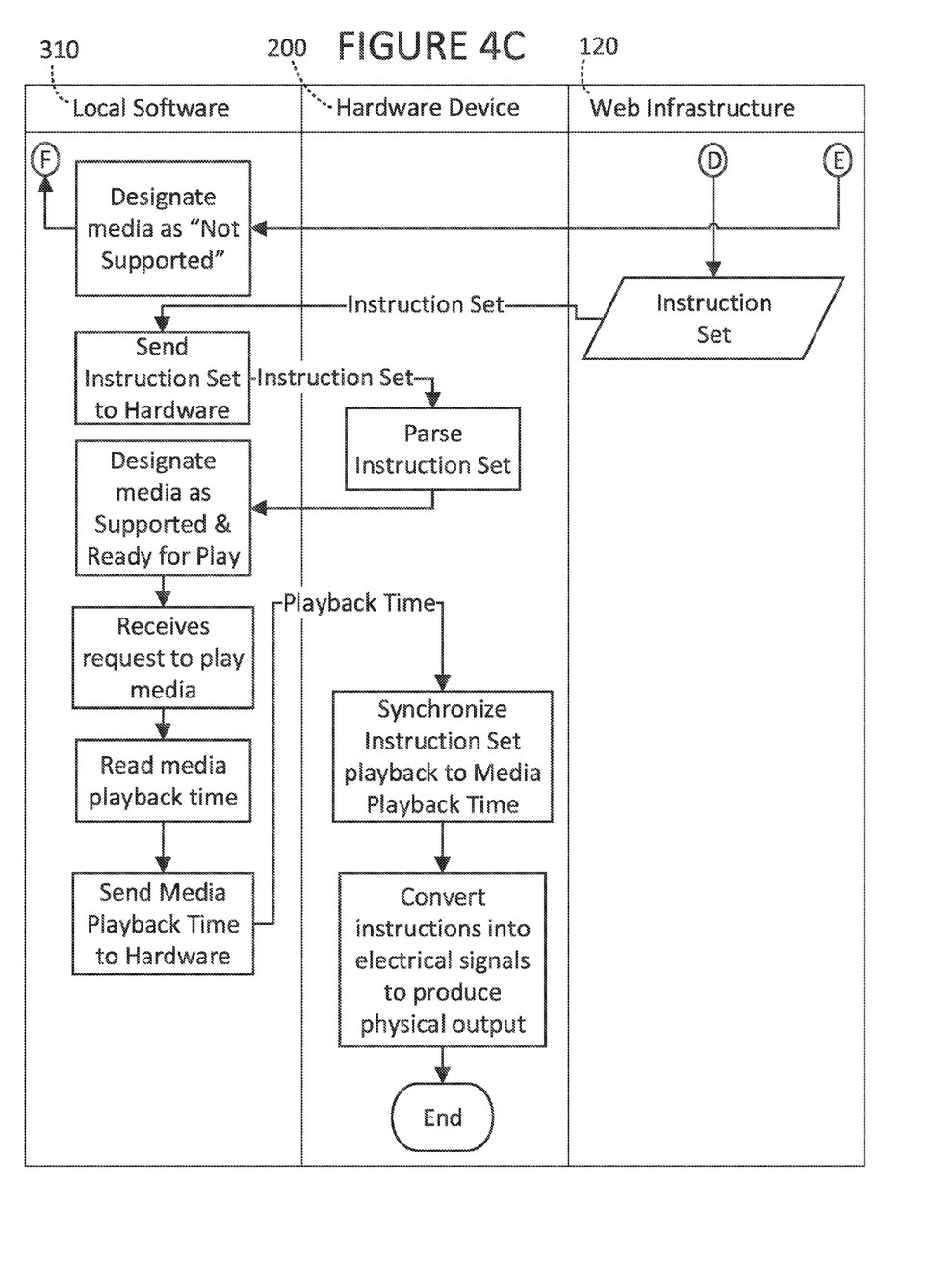

FIG. 4 shows a beginning-to-end process view of the disclosed systems and methods, wherein the instruction set processing occurs within the Local Hardware 200.

A User connects the Local Hardware Device 200 to the Local Computer 100 via the Local Hardware Device's 200 Communication Device 210. Once the Local Hardware Device 200 is connected to the Local Computer 100, the User launches the Local Software 310. The Local Software 310 prompts the User to log in to their account; if an account has not been established, the User is prompted to create a new account. Credentials are passed from the Local Software 310 to the Web Infrastructure 120, which validates the authentication attempt.

Once authenticated, the Local Software 310 detects the Local Hardware Device 200, requests the Local Hardware Device's 200 unique hardware ID, and verifies with the Web Infrastructure 120 that the specific Local Hardware Device 200 is associated with a currently-authenticated account. If so, the Local Software 310 initiates the Local Hardware Device 200. When initialized, the Local Hardware Device 200 is ready to receive current media playback times from the Local Software 310 and the User is notified that the Local Hardware Device 200 is ready for use.

If the unique hardware ID is not associated with an authenticated account, the Web Infrastructure 120 checks to see if it is associated with another account. If it is, the Local Software 310 prompts the User to log in to the correct account to be able to use the connected device; in at least some illustrative embodiments, the usage of simultaneous multiple account logins may be allowed to permit the usage of multiple devices. If the unique hardware ID is not associated with any accounts, the User is prompted to register the unique hardware ID with their account. Once the Local Hardware Device 200 is registered or the User is authenticated to the correct account, the Local Software 310 verifies again with the Web Infrastructure 120 that the specific Local Hardware Device 200 is associated with a currently-authenticated account. The Local Software 310 then initiates the Local Hardware Device 200 and notifies the User that the Local Hardware Device 200 is ready for use.

The User then uses the Local Software 310 to navigate to a web page. Each time a new web page is loaded, the Local Software 310 parses the page to detect supported media. If supported media is not found, the Local Software 310 does nothing; if supported media is found, the Local Software 310 detects and sends the media file information to the Web Infrastructure 120. The Web Infrastructure 120 queries the Database Infrastructure 140 to determine if a hardware instruction set exists for the detected media. If an instruction set is not found, the Local Software 310 designates the media as "not supported;" if an instruction set is found, the Local Software 310 designates the media as "supported & ready for play," and the instruction set file is passed through the Local Software 310 to the Local Hardware 200 for parsing and playback. The designation of "supported & ready for play" and "not supported" may exist as a visual indicator on or near the media file within the web page.

The User then plays the media. The Local Software 310 reads the current playback time of the media and sends that information to the Local Hardware 200. The hardware instruction set contains time flags to mark the accurate playback time of the Haptic Feedback Capable Components 240; the Local Software 310 monitors the accurate playback time of the media, and the Local Hardware 200 uses the media's current playback time and the time flags within the hardware instruction set to maintain synchronization of the Haptic Feedback Capable Components 240 and the media. If the current playback time of the media is adjusted by the User, the Local Software 310 sends the updated current playback time to the Local Hardware 200, which uses the time flags in the hardware instruction set to re-establish synchronization based on the adjustment made by the User. In other embodiments, the playback time may be determined by analyzing the content using computer vision as discussed above.

When the Local Hardware 200 receives the current playback times from the Local Software 310, the Local Hardware 200 interprets said instructions and generates corresponding electrical signals that are sent to the Haptic Feedback Capable Components 240, resulting in the production of physical haptic feedback output that is experienced by the User.

When the User stops the playback of the media the Local Software stops the playback of the hardware instruction set and sends a stop signal to the Local Hardware 200, which stops sending electrical signals to the Haptic Feedback Capable Components 240. The system is then ready for navigation to the next web page, or, if the User disconnects the Local Hardware 200, all memory is cleared and the Local Software 310 is rendered dormant until the Local Hardware 200 is connected again.

Third Illustrative Embodiment

Figure 5A:
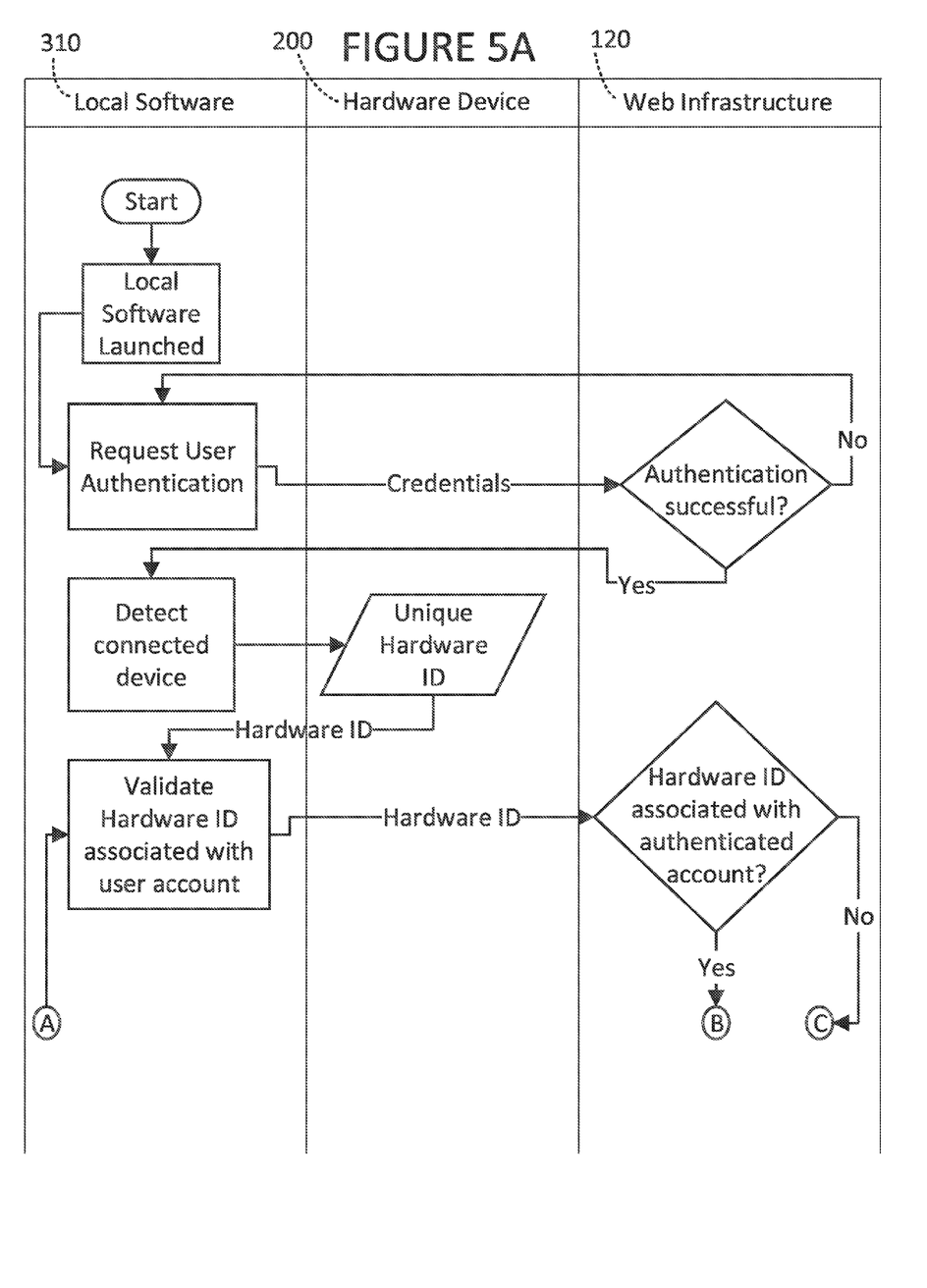
FIGS. 5A-5C show a software flowchart and functional distribution for a third illustrative embodiment.
Figure 5B:
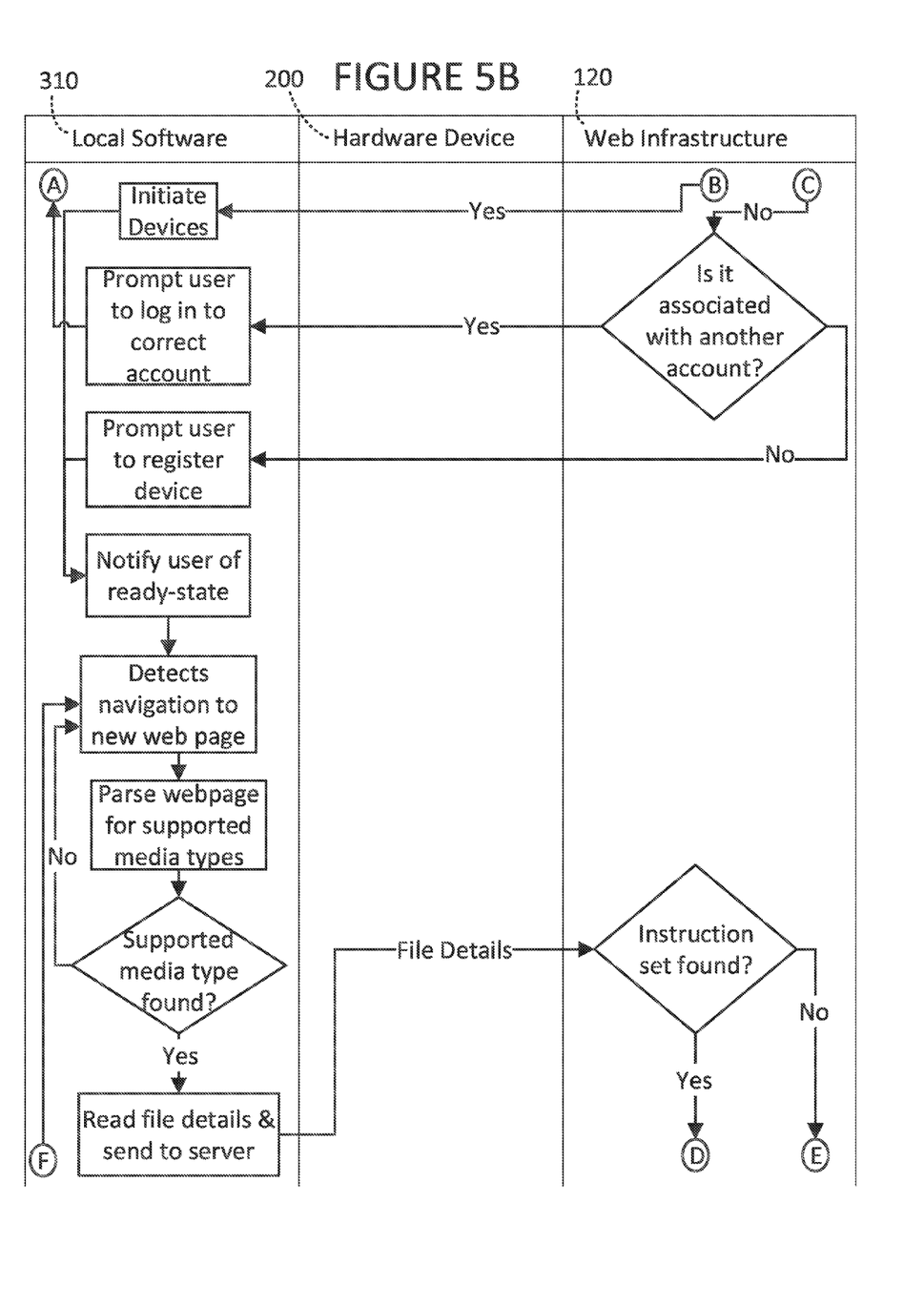
Figure 5C:
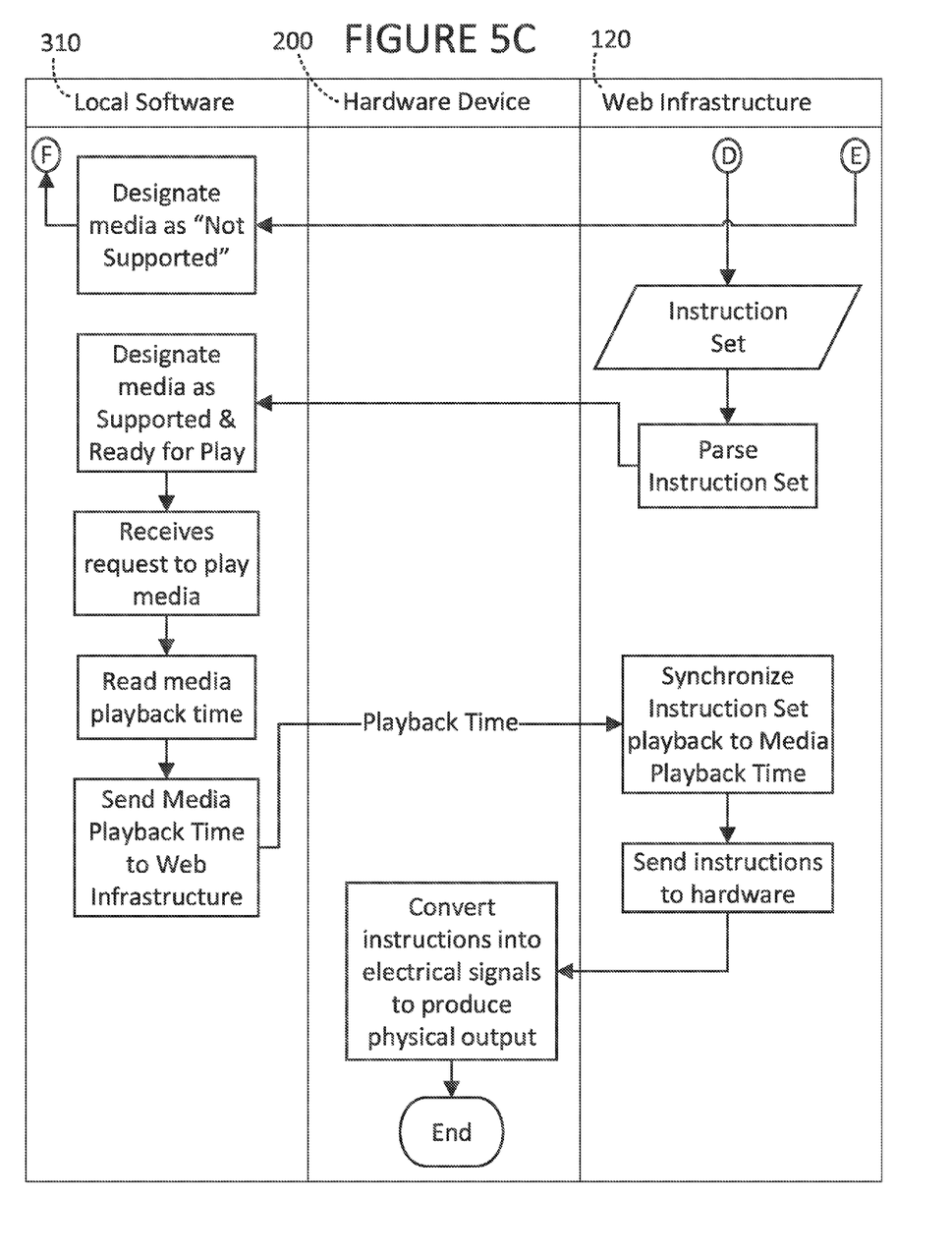

FIG. 5 shows a beginning-to-end process view of the disclosed systems and methods, wherein the instruction set processing occurs within the Web Infrastructure 120.

A User connects the Local Hardware Device 200 to the Web Infrastructure 120 via the Local Hardware Device's 200 Communication Device 210. Once the Local Hardware Device 200 is connected to the Web Infrastructure 120, the User will launch the Local Software 310. The Local Software 310 receives confirmation from the Web Infrastructure 120 that the Local Hardware is connected and prompts the User to log in to their account; if an account has not been established, the User is prompted to create a new account. Credentials are passed from the Local Software 310 to the Web Infrastructure 120, which validates the authentication attempt.

Once authenticated, the Web Infrastructure 120 detects the Local Hardware Device 200, requests the Local Hardware Device's 200 unique hardware ID, and verifies that the specific Local Hardware Device 200 is associated with a currently-authenticated account. If so, the Web Infrastructure 120 initiates the Local Hardware Device 200. When initialized, the Local Hardware Device 200 is ready to receive instructions from the Web Infrastructure 120 and the User 300 is notified that the Local Hardware Device 200 is ready for use.

If the unique hardware ID is not associated with an authenticated account, the Web Infrastructure 120 checks to see if it is associated with another account. If it is, the Local Software 310 prompts the User to log in to the correct account to be able to use the connected device; in at least some illustrative embodiments, the usage of simultaneous multiple account logins may be allowed to permit the usage of multiple devices. If the unique hardware ID is not associated with any accounts, the User is prompted to register the unique hardware ID with their account. Once the Local Hardware Device 200 is registered or the User is authenticated to the correct account, the Local Software 310 verifies again with the Web Infrastructure 120 that the specific Local Hardware Device 200 is associated with a currently-authenticated account. The Local Software 310 then notifies the Web Infrastructure 120 to initiate the Local Hardware Device 200 and the User is notified that the Local Hardware Device 200 is ready for use.

The User then uses the Local Software 310 to navigate to a web page. Each time a new web page is loaded, the Local Software 310 parses the page to detect supported media. If supported media is not found, the Local Software 310 does nothing; if supported media is found, the Local Software 310 detects and sends the media file information to the Web Infrastructure 120. The Web Infrastructure 120 queries the Database Infrastructure 140 to determine if a hardware instruction set exists for the detected media. If an instruction set is not found, the Local Software 310 designates the media as "not supported;" if an instruction set is found, the Local Software 310 designates the media as "supported & ready for play," and the Web Infrastructure 120 retrieves the instruction set file for parsing and playback. The designation of "supported & ready for play" and "not supported" may exist as a visual indicator on or near the media file indicator (e.g., an icon) within the web page.

The User then plays the media. The Local Software 310 reads the current playback time of the media and sends that information to the Web Infrastructure 120. The hardware instruction set contains time flags to mark the accurate playback time of the Haptic Feedback Capable Components 240; the Local Software 310 monitors the accurate playback time of the media, and the Web Infrastructure 120 uses the media's current playback time and the time flags within the hardware instruction set to maintain synchronization of the Haptic Feedback Capable Components 240 and the media. If the current playback time of the media is adjusted by the User, the Local Software 310 sends the updated current playback time to the Web Infrastructure 120, which uses the time flags in the hardware instruction set to re-establish synchronization based on the adjustment made by the User 300. In other embodiments, the playback time may be determined by analyzing the content using computer vision as discussed above.

When the Local Hardware 200 receives the current instructions from the Web Infrastructure 120, the Local Hardware 200 interprets said instructions and generates corresponding electrical signals that are sent to the Haptic Feedback Capable Components 240, resulting in the production of physical haptic feedback output that is experienced by the User.

When the User stops the playback of the media event, the Local Software sends a stop signal to the Web Infrastructure 120. Web Infrastructure 120 in turn sends a stop signal to the Local Hardware 200, which stops sending electrical signals to the Haptic Feedback Capable Components 240. The system is then ready for navigation to the next web page, or, if the User disconnects the Local Hardware 200, all memory is cleared and the Local Software 310 is rendered dormant until the Local Hardware 200 is connected again.

In an alternate embodiment, all of the Local Software 310 functions may exist entirely within the Web Infrastructure 120, and the User may access the disclosed system via a web browser.

Further aspects of the disclosed systems and methods are also disclosed that may be used individually or in combination with the illustrative embodiments previously discussed. In one embodiment, a haptic feedback system is disclosed that includes a processor coupled to a memory and at least one haptic feedback device in communication with the processor. The haptic feedback system may also include a presentation device adapted to present the media content to the user. The processor is configured to execute computer executable instructions, including synchronizing media content loaded on a first computer with instructions received from a second computer. As detailed in the embodiments, above, the media content may be supported media content identified on a particular webpage. In one example, the processor is configured to identify the uniform resource locator of a particular webpage, and the URL is used to identify the media content for the purpose of determining whether the particular media content is supported by the system, i.e. whether the media content has a corresponding instruction set. In other examples, media content may be identified by a serial number or other unique indicia accessible to the system that may be correlated to an instruction set for the media content. In yet other embodiments, the system may interface with a media player and receive information identifying the media content from the media player, such as through a programmatic interface.

In another aspect, the haptic feedback system includes at least one haptic feedback device that includes a hardware identification. In embodiments, the system uses the hardware identification in combination with the identification of the media content to determine whether an instruction set exists for a given media content and haptic feedback device. In this manner, the presently disclosed systems and methods may provide instructions for multiple different haptic devices capable of use with a given media content. In addition, instructions for new or additional haptic devices may be added to the system, reducing the costs associated with supporting multiple devices. In yet other embodiments, the instruction set may contain multiple instruction sets associated with a media content or a haptic device, which are used in combination to generate the desired operation. Because the instructions are stored on a different computer than the media content, a wider variety of media and haptic devices may be supported than was possible with prior integrated systems that included haptic commands embedded in the media content.

The identification of the haptic device may occur at various times during operation of the system. In one example, when an internet browser is launched, the haptic device is automatically detected and a determination made as to whether the device is supported. In other embodiments, a user is permitted to provide the identification of the haptic device. In yet other embodiments, the haptic device may be a plug-and-play device, which is automatically identified when connected to a computer. Other methods of identifying the haptic device are also possible and are contemplated for use with the presently disclosed systems and method.

In various embodiments, the haptic feedback system synchronizes the media content with the instructions. The synchronization may be achieved using the current playback time of the media content as previously discussed, which may be accessed from the media player. In some embodiments, the media content may be parsed into scenes or frames of a defined duration, and the instructions synchronized to such scenes or frames as desired. Either prior to or after synchronization with the media content, the instructions are converted into one or more electrical signals used to control the at least one haptic feedback device. One of ordinary skill in the art will appreciate that the transformation of instructions into electrical signals may be performed in a variety of ways using conventional computing equipment, including processors and hardware drivers located in a computer, in a given haptic device or allocated between multiple components. In any event, the at least one haptic device is configured to receive the one or more electrical signals and to provide physical stimulations to a user accessing the content in synchronization with the playback of the media content. In embodiments, haptic device may be immediately responsive to the electrical signals, or alternatively, the haptic device may store the electrical signals as instructions to be applied when triggered by the haptic feedback system.

The haptic feedback systems and methods presently disclosed may be applied in a wide range of applications. For example, the haptic feedback device may be a game controller adapted for use with an online video game system. The game controller may provide physical stimulation corresponding to actions occurring within the game content to enhance the user experience. In other embodiments, the haptic device may be by a sexually oriented hardware device or other entertainment related device. In yet other embodiments, the haptic feedback system may be applicable to training or education applications, such as surgical training simulators that benefit from physical stimulations to simulate real life operating procedures. These and other applications will be apparent to persons of ordinary skill in the art and these examples are provided solely to help illustrate the breadth of applications for the haptic feedback systems and methods.

Numerous other modifications, equivalents, and alternatives, will become apparent to those skilled in the art once the above disclosure is fully appreciated. For example, while the disclosed embodiments are described within the context of a system used to augment a multimedia event for entertainment purposes, other embodiments may include systems used in the rehabilitation of patients suffering from, for example, reduced physical and/or sexual function such as that caused by the side-effects of diabetes, traumatic brain injuries, spinal cord injuries and/or prostate-related issues. It is intended that the following claims be interpreted to embrace all such modifications, equivalents, and alternatives where applicable.

What is claimed is:

1. A method for multimedia tactile augmentation, comprising:
   identifying media content loaded on a first computer;
   retrieving hardware identifying information of at least one haptic feedback device connected to the first computer;
   locating instructions stored on a second computer, said instructions corresponding to the content and to the hardware identifying information of the at least one haptic feedback device;
   initiating playback of the content;
   synchronizing the instructions with the content;
   parsing and converting the instructions into one or more electrical signals;
   driving the at least one haptic feedback device with the electrical signals in synchronization with the playback of the content, the at least one haptic feedback device providing physical stimulation to a user accessing the content; and
   presenting the content to the user.

2. The method of claim 1, wherein the parsing and synchronizing are performed by the first computer and the converting is performed by a processing unit coupled to the at least one haptic feedback device.

3. The method of claim 1, wherein the parsing, synchronizing and converting are performed by a processing unit coupled to the at least one haptic feedback device.

4. The method of claim 1, wherein the parsing and synchronizing are performed by the second computer and the converting is performed by a processing unit coupled to the at least one haptic feedback device.

5. The method of claim 1, further comprising the second computer providing access to the instructions via the Internet through a web interface presented on the first computer.

6. A method for multimedia tactile augmentation, comprising:
   identifying media content within a first file loaded on a computer;
   retrieving hardware identifying information of at least one haptic feedback device connected to the first computer;

locating instructions within a second file loaded on the computer, said instructions corresponding to the content and to the hardware identifying information of at least one haptic feedback device;

initiating playback of the content;

synchronizing the instructions with the content;

parsing and converting the instructions into one or more electrical signals;

driving the at least one haptic feedback device with the electrical signals in synchronization with the playback of the content, the at least one haptic feedback device providing physical stimulation to a user accessing the content; and presenting the content to the user.

7. A haptic feedback system comprising:

a processor coupled to a memory, the processor configured to execute the following computer-executable instructions stored in the memory:

retrieving hardware identifying information of at least one haptic feedback device connected to a first computer;

synchronizing media content loaded on the first computer with instructions received from a second computer, said instructions corresponding to the media content and to the hardware identifying information of the at least one haptic feedback device, and converting the instructions into one or more electrical signals; and at least one haptic feedback device in communication with the processor, wherein the at least one haptic feedback device is configured to receive the one or more electrical signals and to provide physical stimulations to a user accessing the content in synchronization with the playback of the media content.

8. The haptic feedback system of claim 7 further comprising:

a presentation device adapted to present the media content to the user.

9. The haptic feedback system of claim 7, wherein the at least one haptic feedback device is further configured to communicate wirelessly with the processor.

10. The haptic feedback system of claim 7, wherein the at least one haptic feedback device further comprises at least one communication device selected from the group consisting of a serial port, a parallel port, a universal serial bus, a BlueTooth device, a near field communication device, and an infrared communication device.

11. The haptic feedback system of claim 7, wherein the at least one haptic feedback device is a game controller adapted for use with an online video game system.

12. The haptic feedback system of claim 7, wherein the at least one haptic feedback device is a sexually oriented hardware device.

* * * * *